United States Patent [19]
Wilson, III

[11] Patent Number: 5,605,164
[45] Date of Patent: Feb. 25, 1997

[54] PROPHYLACTIC DEVICE AND PRODUCTION OF SAME

[75] Inventor: Thomas W. Wilson, III, Chapel Hill, N.C.

[73] Assignee: Family Health International, Durham, N.C.

[21] Appl. No.: 487,712

[22] Filed: Jun. 7, 1995

[51] Int. Cl.$^6$ ............................................. A61F 6/02
[52] U.S. Cl. ............................................. 128/842; 602/60
[58] Field of Search .................................. 128/842, 844, 128/918; 604/347–359; 602/3, 60–62

[56] References Cited

U.S. PATENT DOCUMENTS

| | | |
|---|---|---|
| D. 253,009 | 9/1979 | Okamoto . |
| 2,285,981 | 6/1942 | Johns . |
| 3,018,484 | 1/1962 | Koehn . |
| 3,085,570 | 4/1963 | Penska . |
| 3,469,685 | 9/1969 | Baermann . |
| 3,536,066 | 10/1970 | Ludwig . |
| 4,004,591 | 1/1977 | Freimark . |
| 4,009,717 | 3/1977 | Allen . |
| 4,095,293 | 6/1977 | Heavner et al. . |
| 4,232,675 | 11/1980 | Meldahl . |
| 4,241,828 | 12/1980 | Bourdelle et al. . |
| 4,275,812 | 6/1981 | Poncy et al. . |
| 4,354,494 | 10/1982 | Hogin . |
| 4,432,357 | 2/1984 | Pomeranz . |
| 4,576,156 | 3/1986 | Dyck et al. . |
| 4,588,397 | 5/1986 | Giacalone . |
| 4,626,250 | 12/1986 | Schneider . |
| 4,684,490 | 8/1987 | Taller et al. . |
| 4,735,621 | 4/1988 | Hessel . |
| 4,784,655 | 11/1988 | Campion et al. . |
| 4,794,920 | 1/1989 | Robichaud . |
| 4,798,600 | 1/1989 | Meadows . |
| 4,808,174 | 2/1989 | Sorkin . |
| 4,817,593 | 4/1989 | Taller et al. . |
| 4,834,113 | 5/1989 | Reddy . |
| 4,855,169 | 8/1989 | McGlothin et al. . |
| 4,863,449 | 9/1989 | Terriault et al. . |
| 4,872,464 | 10/1989 | Loeb et al. . |
| 4,875,490 | 10/1989 | Quiroz . |
| 4,875,491 | 10/1989 | Parrone . |
| 4,888,007 | 12/1989 | Loeb et al. . |
| 4,942,885 | 7/1990 | Davis et al. . |
| 4,954,309 | 9/1990 | McGlothlin et al. . |
| 4,955,392 | 9/1990 | Sorkin . |
| 4,961,734 | 10/1990 | Kassman . |
| 4,964,416 | 10/1990 | Foldesy et al. . |
| 4,966,166 | 10/1990 | Leffler . |
| 5,065,771 | 11/1991 | Ferguson . |
| 5,112,900 | 5/1992 | Buddenhagen et al. . |
| 5,176,152 | 1/1993 | Wheeler ................................ 128/844 |
| 5,181,527 | 1/1993 | Dorsey et al. . |
| 5,205,298 | 4/1993 | Hurst .................................... 128/844 |
| 5,269,320 | 12/1993 | Hunnicutt . |
| 5,351,698 | 10/1994 | Wheeler et al. . |
| 5,398,699 | 3/1995 | Fergus ................................... 128/844 |
| 5,429,141 | 7/1995 | Korsinsky et al. . |
| 5,458,114 | 10/1995 | Herr ...................................... 128/842 |

*Primary Examiner*—Michael A. Brown
*Attorney, Agent, or Firm*—Richard S. Faust

[57] ABSTRACT

A prophylactic device is described which is constructed primarily from portions of plastic film material alternatingly sealed at their periphery and at an aperture contained in the film to yield an accordion-like section. The prophylactic device, as manufactured, is relatively flat, but it can expand to cover a body part to provide protection from transmission of bodily fluids between individuals. The prophylactic device can be used as a glove-like device, a finger cot, a condom, or a wound covering, depending on the size and configuration of the device.

19 Claims, 5 Drawing Sheets

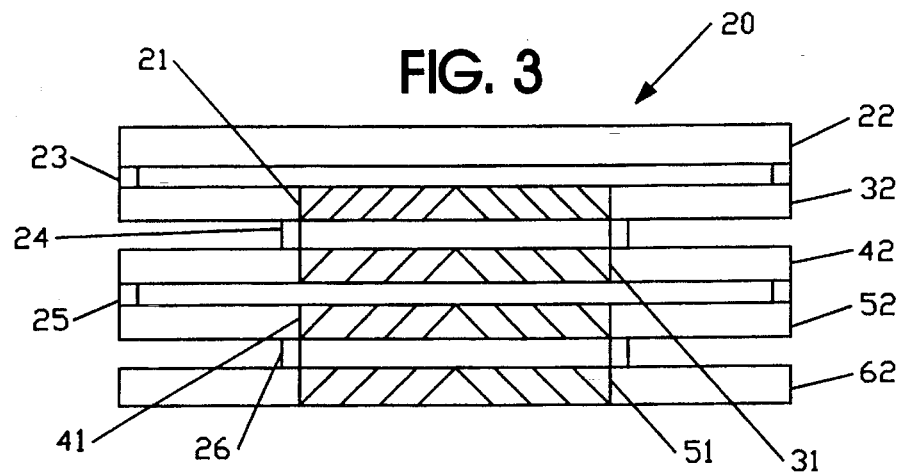
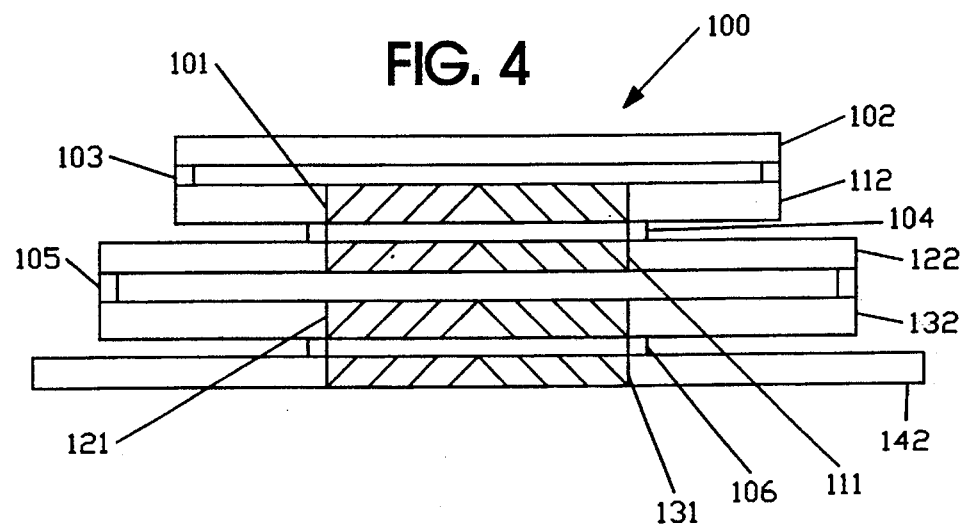
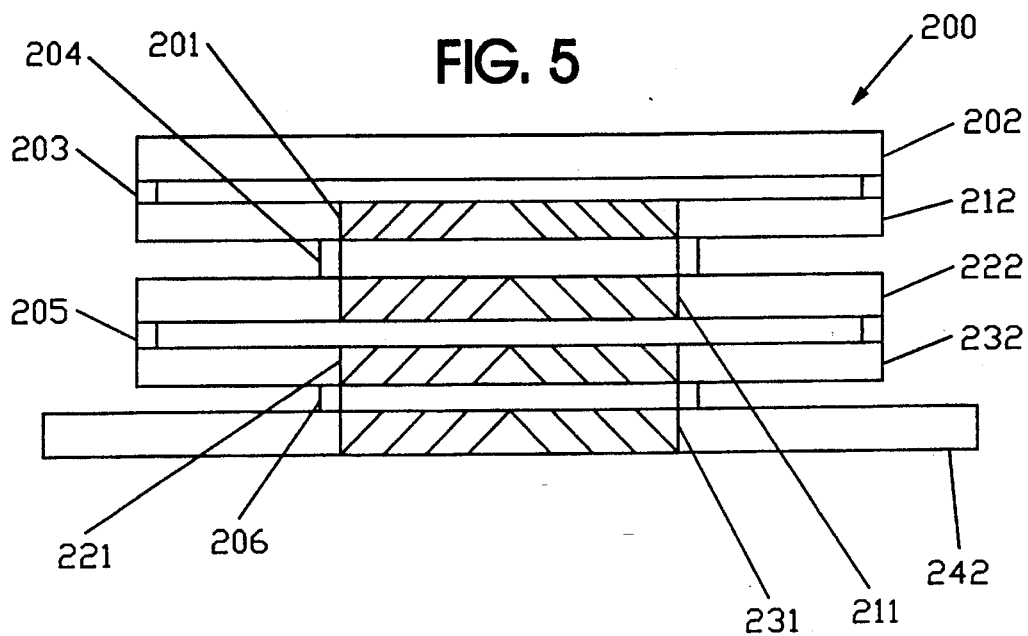

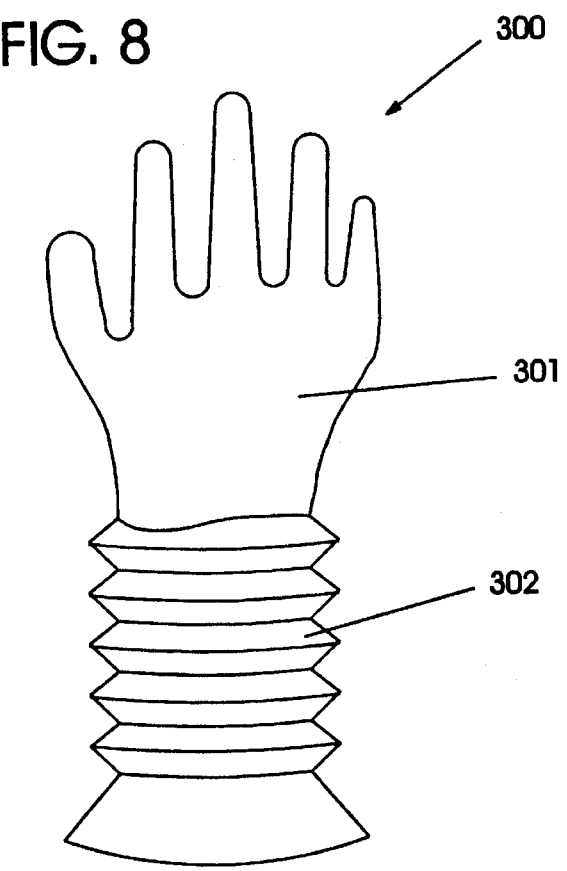
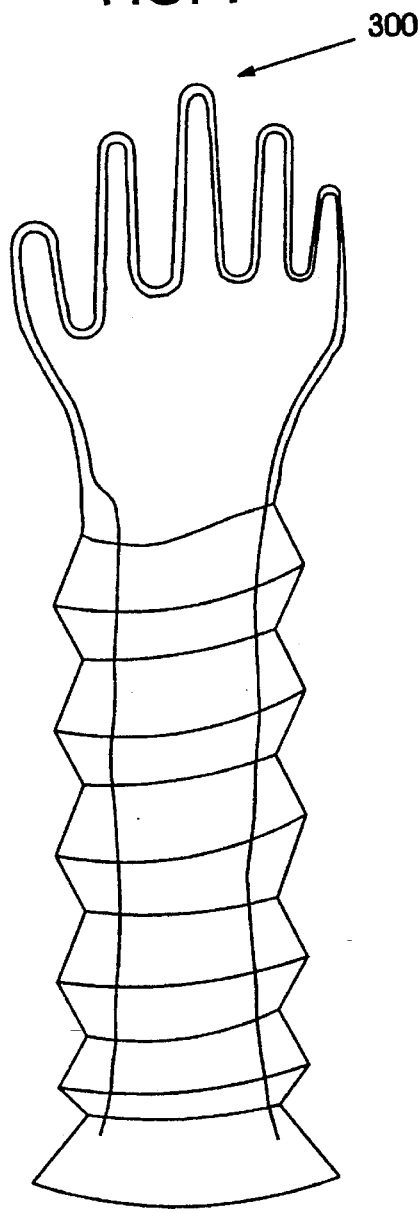
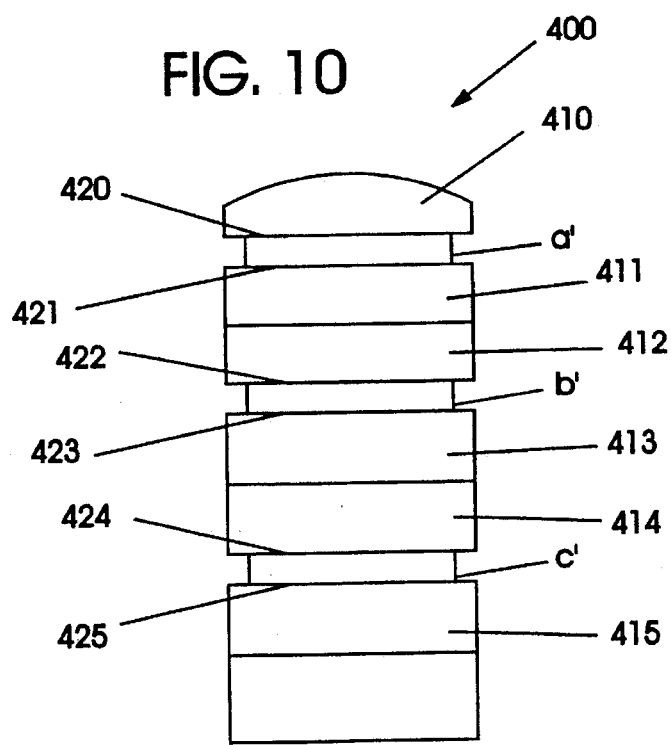

PROPHYLACTIC DEVICE AND PRODUCTION OF SAME

GOVERNMENT LICENSE RIGHTS

The invention claimed herein was made under one or more of the following contracts: U.S. Agency for International Development Contract Nos. DPE-3041-A-00-0043 and DPE-0537-A-00-4047, and National Institutes of Health Contract No. N01-HD-2-3143, and the U.S. government has certain rights therein.

FIELD OF THE INVENTION

This invention relates to an improved construction for a prophylactic device, such as a condom or finger cot. Specifically, the invention provides an accordion-like prophylactic sheath formed from pieces of plastic film with concentrically aligned apertures.

DESCRIPTION OF THE RELATED ART

Prophylactic devices, such as condoms, gloves and finger cots, have increased greatly in usage due to the prevalence of AIDS, other sexually transmitted diseases, hepatitis, and a plethora of hazardous, blood-borne pathogens. Most prophylactic devices are formed from vulcanized latex rubber, obtained primarily from *Hevea brasiliensis*. Latex rubber has great advantages in elasticity and strength, but a certain portion of the population has become allergic to latex rubber, i.e. either to proteins inherent in the latex or to chemicals utilized in the processing of the raw latex into a rubber article. The increased use of latex rubber gloves in medical procedures has increased the prevalence of allergic reactions in health care workers and in the general populace. The nature of the allergic reactions ranges from simple urticaria to anaphylactic shock, causing several deaths each year. Consequently, the use of alternate materials in prophylactic devices has been a major focus. These alternate materials, usually thermoplastic elastomers, do not possess the extreme elongations at low forces and almost 100% recovery from deformation that are inherent in latex rubber. To create effective prophylactic devices, especially condoms, it is necessary to employ modified designs from the traditional form-fitting cylindrical sheath to compensate for the sometimes limited physical/mechanical properties of the materials of construction.

Standard latex prophylactic devices are made by a dipping process, whereby an appropriately dimensioned mold is dipped into a latex rubber emulsion formulated with various curing (vulcanizing) agents and accelerators. The mold, coated with the latex rubber emulsion, is withdrawn and subjected to elevated temperatures for drying and curing of the latex to achieve the desired physical properties. In the case of condoms and finger cots, the cured device is stripped from the mold and rolled into a toroidal configuration. For condoms, the presentation to the consumer is in the familiar toroidal roll configuration and the condom is donned by unrolling it down the shaft of the penis. A great disadvantage of latex condoms is that the rolled configuration is sometimes difficult for the consumer to orient correctly. If the consumer places the condom on incorrectly, it will not unroll. If the consumer subsequently reorients the condom, i.e. flips it over, and unrolls it, then bodily fluids may be transmitted to the recipient coital partner resulting in possible transmission of diseases or sperm.

Non-latex, plastic condoms have been made by a dipping process, as described in U.S. Pat. No. 4,855,169. A mold is dipped into a solution of an elastomer dissolved in a volatile solvent. The mold is withdrawn from the solution and the solvent is evaporated. A band of material is incorporated into the device at the open (proximal) end to facilitate rolling of the condom into the typical toroidal roll configuration. This condom is donned in an analogous manner to rolled latex rubber condoms, and it is a form-fitting condom with its primary means of retention being the compressive force it exerts along the length of the penis.

Other condoms from plastic films have been made by incorporating a sealing aperture (U.S. Pat. No. 4,964,416) into the proximal end of a sheath or attaching two sealing apertures to the proximal end of a separately formed sheath (U.S. Pat. No. 5,351,698). The '416 and '698 condoms are not form-fitting, but are a baggy sheath with the retention being provided by the sealing aperture(s) bearing compressively only at the base of the penis.

Another condom which has an unusual expander portion is described in U.S. Pat. No. 5,398,699. In addition to an expander portion, the condom also contains a greatly enlarged portion in close proximity to the open (proximal) end to encase the testicles. The enlarged portion tapers to the open end, thus providing retention of the condom on the penis by entrapment of the testicles. The condom is presumably formed via a dipping and curing or drying process from silicone rubber. It cannot be packaged flat and may not be able to be rolled.

A garment shaped like a bikini with a proboscis is described in U.S. Pat. No. 3,536,066. The proboscis is made from a number of bellows-like sections and can collapse to a non-extended configuration. The proboscis can extend either inwardly toward the user or outwardly if used by a male.

SUMMARY OF THE INVENTION

The present invention provides a prophylactic device formed from pieces of plastic film. Instead of the traditional cylindrical, tubular configuration, the device of the invention is formed from a plurality of pieces of film attached to one another so that the device can expand in an accordion-like fashion to fit a wide variety of body parts, while being collapsible to a flat, compact form. The initially flat device uses the material of the pieces of film, extending from the aperture to the outer edge of each piece, to provide the material for expansion of the device with the minimal diameter of the device being loosely defined by the apertures. The device is most conveniently made by using disk-shaped pieces of film with concentrically aligned apertures, but any shape of film pieces or apertures may be suitable for construction of prophylactic devices according to the present invention.

In one aspect, the present invention may be defined as a prophylactic device constructed from a plurality of joined, superposed disks (circular configuration) of film containing concentrically aligned apertures in which the peripheral edge of the aperture of one disk is sealed to the peripheral edge of the aperture of an adjacent disk and the outer edge of the adjacent disk is sealed to the outer edge of the next disk in line, thus forming a structure analogous to an accordion-folded structure. A terminal disk, without an aperture, is connected to one end of the series of joined disks to provide an enclosure to the device.

The disks can be formed from any suitable elastic and flexible film materials that can be joined together to form a defect-free sealed region. Typically, thermoplastic elastomeric film materials, which are heat-sealed together, make an ideal product and process for construction of the prophylactic device. Thickness of the film material is not a critical concern, but for certain applications requiring transmission of tactile sensations, thicknesses of less than 1 mm (0.04") are preferred.

The superposed disks can be of the same external diameter to produce a very uniform device. Alternatively, the disks may have varying external diameters. For example, the terminal disk and the next adjacent disk, which are joined around their respective peripheral edges, should have the same external diameter, but the next two adjacent disks can be of greater or lesser external diameter. Another variation of the above can be constructed by making each disk, except for the disk at the proximal end, of the same external diameter. The disk at the proximal end may have a greater external diameter, thus providing "grips" to aid in donning the device. It may also be of thicker film to provide a greater retention surface.

As the external diameter of the disks can be varied, so can the diameters of the apertures. In a finger cot application, the diameter of the apertures can increase from the distal end with each successive section, thereby creating a comfortable and conformable product with a number of sealing elements where the aperture seals engage the finger. In a condom application, the apertures can be the same size, or the aperture closest to the distal end of the condom can be slightly smaller to provide a secure "locking" type engagement when the condom is drawn over the glans of the penis.

Another application for the prophylactic device described herein is a large glove type structure. This device may have an actual glove attached to the end of the accordion-folded structure, or it may simply be a baggy structure of accordion-folded sections. A glove type structure such as described above is useful in emergency situations when large numbers of trauma victims need to be handled and moved quickly before treatment and bandaging. The glove type structure can cover the entire arms of rescue workers, and thus protect them from blood-borne contaminants. These gloves are inexpensive, durable, easily changed, and require minimal space for storage. Due to the expandable nature of the product, the gloves can adapt to a wide variety of arm lengths and diameters.

Another use for the glove type structures is as a wound covering or dressing. The product can be quickly slipped over an arm or leg and protect the appendage from dirt or further contamination, if the victim has to be moved. This also provides protection to the rescue worker, as it isolates the blood and tissues of the victim. Such a device made from clear plastic permits the rescue worker to observe the wound to see if further immediate treatment is necessary.

Another aspect of the present invention is a method for making the expandable and collapsible devices rapidly and easily from thin polymeric film materials. According to a preferred manner of carrying out the invention, several layers of film are carried together by an indexing conveyor system that maintains registration between the layers of film. The film layers which require the apertures are cut in one step (for a single aperture size) or several steps (for multiple aperture sizes). The film layers, with the apertures in substantially concentric registration, are indexed to the next processing step. In the next processing step, a series of sealing and cutting rings are positioned between the layers of film, above the top layer of film and/or below the bottom layer of film. Next, a mandrel containing slidable flanges with, for example, heat sealing surfaces translates through the apertures. The diameter of the mandrel is substantially the same as the diameter of the apertures in the film layers. The slidable flanges on the mandrel are of slightly larger diameter than the diameter of the apertures. The slidable flanges pass through the apertures and the elastic nature of the film layers allows them to "snap" lock into the spaces between the slidable flanges. The sealing and cutting can be accomplished in a single step or through several progressive steps. In the single step process, the slidable flanges on the mandrel mate and effect a seal around the peripheries of the top aperture to the second aperture, the third aperture to the fourth aperture, the fifth aperture to the sixth aperture, and so forth; concurrently, the sealing and cutting rings mate and effect a seal and cut, thus creating the end disk, which does not contain an aperture, and connecting the end disk to the first disk, which does contain an aperture, then the second and third disks are created and sealed together, then the fourth and fifth disk are created and sealed together, and so forth, with the last disk being cut and releasing the finished product from the layers of film. The product, if manufactured in a single step, is retained on the mandrel and can be ejected via air pressure through the mandrel tip or a vacuum tube above the mandrel. Note that the mandrel has to be withdrawn to index the next sections of film, but the sealing and cutting rings may remain between the layers of film. Also the last disk at the proximal end of the prophylactic device can be cut in a separate, subsequent operation so that the finished product can be carried along on the film material to a next processing station. The next processing station might, for example, contain means for leak detection of the product or packaging of the product.

The prophylactic device, as described above, is most conveniently constructed from an odd number of film pieces. However, prophylactic devices may be manufactured from an even number of film sections, i.e. four or more, with the two sections closest to the proximal end aiding in the donning of the prophylactic device. A prophylactic device of this construction may have certain advantages in that a double seal, or fluid dam, exists at the proximal end.

The invention is described herein primarily in terms of disk-shaped pieces of film for ease of explanation and visualization, but it will be appreciated pieces of any shape may be used to form the prophylactic device of the present invention. The collapsible nature of the product allows for convenient storage in a flat configuration. The ability to store the prophylactic device in a flat configuration provides less stress on the device during storage. The several apertures of the device allow for multiple sealing surfaces to prevent slippage and multiple fluid dams to prevent leakage of fluid, which are desirable attributes in, for example, a condom application.

BRIEF DESCRIPTION OF THE DRAWINGS

FIG. 3 is a side view in cross-section of a device with equally sized apertures and equally sized disks.

FIG. 4 is a side view in cross-section of a device with equally sized apertures and differently sized disks.

FIG. 5 is a side view in cross-section of a device with equally sized apertures and equally sized disks, except for the proximal end disk.

FIG. 8 is a side view of a device with a glove attached to one end.

FIG. 9 is a pictorial view of a glove-like device shown over an arm.

FIG. 10 is a side view of a mandrel with slidable flanges useful in the production of prophylactic devices of the invention.

FIG. 11 is a side view of a set of sealing and cutting rings with film threaded between.

DETAILED DESCRIPTION OF THE INVENTION AND PREFERRED EMBODIMENTS THEREOF

Figure 1:
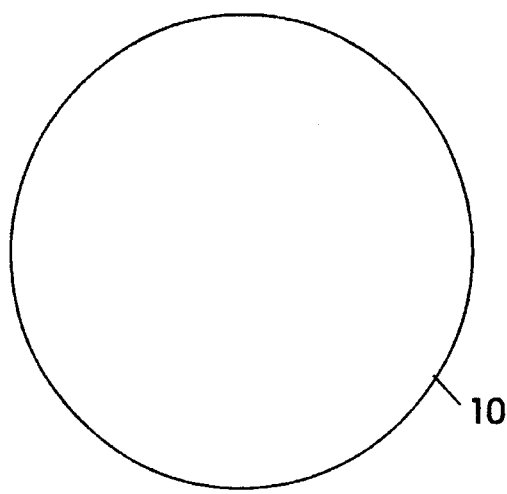
FIG. 1 is a top view of an end disk that serves as the distal end piece for a prophylactic device of the invention.

The present invention is based on the discovery that multiple layers of film can be easily joined in a unique fashion such that they will collapse to a small, predominantly flat and unstressed structure for storage and packaging and can be subsequently expanded to overfit portions of a human body for the purpose of prophylaxis. Anticipated uses of the above construction are finger cots, condoms, gloves and wound dressings. Other uses will be apparent to those skilled in the art.

The material employed in the construction should be flexible to permit sufficient movement without binding or undue friction on the body parts of the wearer. The material should be sufficiently elastic to permit expansion of the device to fit a wide variety of sizes of body parts. For the most effective and efficient manufacture of devices, the material should be available in a continuous film form. Also, the material should be easily bonded to itself by heat, ultrasound, chemical or mechanical methods.

Suitable materials are thermoplastic elastomers, such as polyurethanes or block copolymers or polyolefins. The preferred polyurethanes contain hard and soft segments and may be polyester urethanes or polyether urethanes or combinations of polyester and polyether urethanes. Block copolymers, such as polystyrene-polyisoprene-polystyrene copolymers and polystyrene-poly(ethylene/butylene)-polystyrene copolymers are suitable materials. Thermoplastic polyolefins can be usefully employed as materials of construction. Other thermoplastic elastomers will be readily apparent to those skilled in the art and may include composites, copolymers and blends of the above.

Other materials, that are not classified as thermoplastic elastomers, may have utility in the construction of certain devices, for example, plasticized polyvinyl chloride, polyvinylidene chloride, polyvinylidene fluoride, polyolefins, polyesters, polyamides and composites, copolymers and blends of the above.

As an example of the simplest form of the device, it can be formed of three pieces of film sealed together. Each piece may, for example, comprise disks of material with two of the three disks having concentrically positioned apertures. The disk without an aperture is sealed around its diametral periphery to one of the two disks with an aperture. Additionally, the two disks with apertures are sealed to each other around the peripheries defined by the apertures.

For a condom application utilizing the above construction of only three disks and assuming an aperture diameter of 3.2 cm (1.25"), two of the disk portions would have to be greater than 19 cm (7.4") in diameter to cover the shaft of the average penis (1.6" diameter and 6" length). Remember that during coitus the disk at the proximal end of the device serves primarily as a pubic shield, and only the two remaining disks form the portion of the device which encases the penis. This device would contain a large excess of material that may bunch up around the penis and cause discomfort to the wearer and to the recipient coital partner and decrease sensitivity for the wearer of the device. If the number of disks is increased to five and assuming equal diameter disks, then the disk diameter to cover the average penis decreases to 11 cm (4.3"). Furthermore, if the number of disks is increased to seven, then the disk diameter to cover the average penis decreases to 8.4 cm (3.3"). A reasonable and practical upper limit is probably nine disks, which yields a diameter of 7.1 cm (2.8") to create a condom which will cover the average penis. Seven disks is the preferred embodiment for a condom, as the size and excess material become unwieldy at less than seven disks and the manufacturing becomes more complicated as the number of disks increases. With seven disks, there are three sealing elements, or fluid dams where the aperture seals may contact the penis. The sealing elements help to prevent leakage of seminal fluid after ejaculation. Furthermore, the sealing elements provide three retention areas; thus, there will be three retention elements which have to be pulled over the glans of the penis to remove the condom during coitus. The condom can be easily removed from the penis after withdrawal from the coital partner following detumescence. The above example is not to be construed as limiting to dimensions or numbers of disks for a condom application.

In a condom application, a great advantage can be attained in donning of the condom by making the proximal piece larger than the other pieces. Two important advantages are that the larger proximal piece provides "grips" to aid in donning, and the larger proximal piece helps the consumer to orient the condom in the proper direction. Unlike rolled latex condoms, it is difficult for the consumer to apply a condom of this invention to the penis in the wrong orientation because as the larger proximal piece is grasped by the consumer, the condom unfolds slightly, thus indicating the correct direction of donning.

For other applications, it is relatively easy for those skilled in the art to determine the number of disks, their diameter(s) and appropriate aperture size(s) to create the desired prophylactic device with the necessary coverage and retention.

The use of disk-shapes in the formation of the apertures and the film sections provides a great advantage in the manufacture of the equipment to make the prophylactic device. Disk-shaped dies are easier and quicker to manufacture than polygonal or irregular shaped dies.

The invention now will be more fully described with reference to the drawings.

FIG. 1 is a top view of an end disk 10 which is employed as the closed distal end of a prophylactic device.

Figure 2:
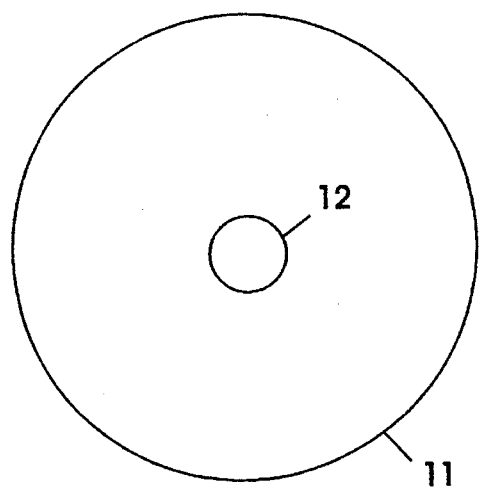
FIG. 2 is a top view of one of the disks with a concentrically aligned aperture.

FIG. 2 is a top view of one of the disks 11 with a concentrically aligned aperture 12. The aperture provides a sealing element in the finished product designed to bear compressively against the sheathed body part.

FIG. 3 is a side view in cross-section of a device 20 with equally sized apertures, which define aperture edges 21, 31, 41, 51, and equally sized disks 32, 42, 52, 62 containing the apertures, and an end disk 22. There is seal 23 joining the outer peripheries of the end disk 22 to the next disk 32. The seal 23 extends around the entire diametral extent of disks 22 and 32. There is seal 24 joining the aperture edges 21 and 31. The seal 24 extends around the entire diametral extent of the aperture edges 21 and 31. There is seal 25 joining the outer peripheries of disk 42 to disk 52. The seal 25 extends around the entire diametral extent of disks 42 and 52. There is seal 26 joining the aperture edges 41 and 51. The seal 26 extends around the entire diametral extent of the aperture edges 41 and 51.

FIG. 4 is a side view in cross-section of a device 100 with equally sized apertures, which define aperture edges 101, 111, 121, 131, and differently sized disks 102, 112, 122, 132, 142. There is seal 103 joining the outer peripheries of the end disk 102 to the next disk 112. The seal 103 extends around the entire diametral extent of disks 102 and 112. There is seal 104 joining the aperture edges 101 and 111. The seal 104 extends around the entire diametral extent of the aperture edges 101 and 111. There is seal 105 joining the outer peripheries of disk 122 to disk 132. The seal 105 extends around the entire diametral extent of disks 122 and 132. There is seal 106 joining the aperture edges 121 and 131. The seal 106 extends around the entire diametral extent of the aperture edges 121 and 131.

The devices in FIGS. 3 and 4 can be continued with additional disks to make a more extended product than that shown. The additional disks can be of greater, lesser or substantially equivalent diametral extent. Also the apertures in the disks can be of greater, lesser or substantially the same diametral extent.

FIG. 5 is a side view in cross-section of a device 200 with equally sized apertures, which define aperture edges 201, 211, 221, 231, and equally sized disks 202, 212, 222, 232, except for the proximal end disk 242 which is of larger diameter than the other disks. There is seal 203 joining the outer peripheries of the end disk 202 to the next disk 212. The seal 203 extends around the entire diametral extent of disks 202 and 212. There is seal 204 joining the aperture edges 201 and 211. The seal 204 extends around the entire diametral extent of the aperture edges 201 and 211. There is seal 205 joining the outer peripheries of disk 222 to disk 232. The seal 205 extends around the entire diametral extent of disks 222 and 232. There is seal 206 joining the aperture edges 221 and 231. The seal 206 extends around the entire diametral extent of the aperture edges 221 and 231. The larger proximal end disk 242 aids in donning the device, and if the device is a condom, then the end disk can serve as a pubic shield to help prevent the transmission of bodily fluids between individuals engaged in intercourse.

Figure 6:
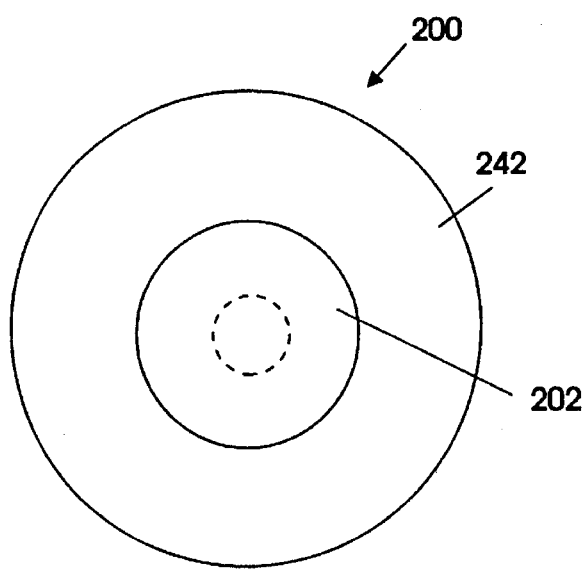
FIG. 6 is a top view of the device in FIG. 5.

FIG. 6 is a top view of device 200 shown in FIG. 5 that contains the larger proximal end disk. It should be noted that the proximal end portion does not need to be disk-shaped. In a condom application, a more triangular shape may be better suited to function as a pubic shield. The concentrically aligned apertures are shown as a dotted outline in the figure.

Figure 6A:
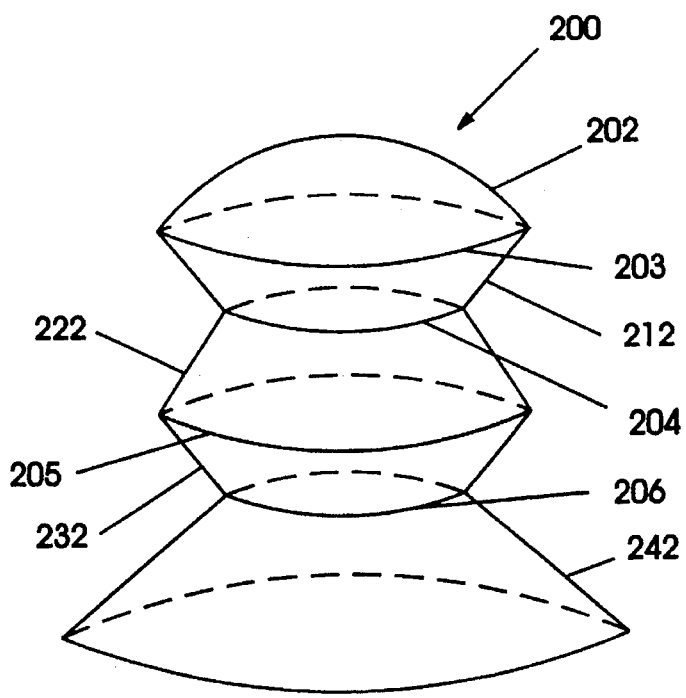
FIG. 6A is a perspective view of the device of FIGS. 5 and 6.

FIG. 6A is a perspective view of device 200 of FIGS. 5 and 6 with the device partially expanded to reveal the accordion-like folds.

Figure 7:
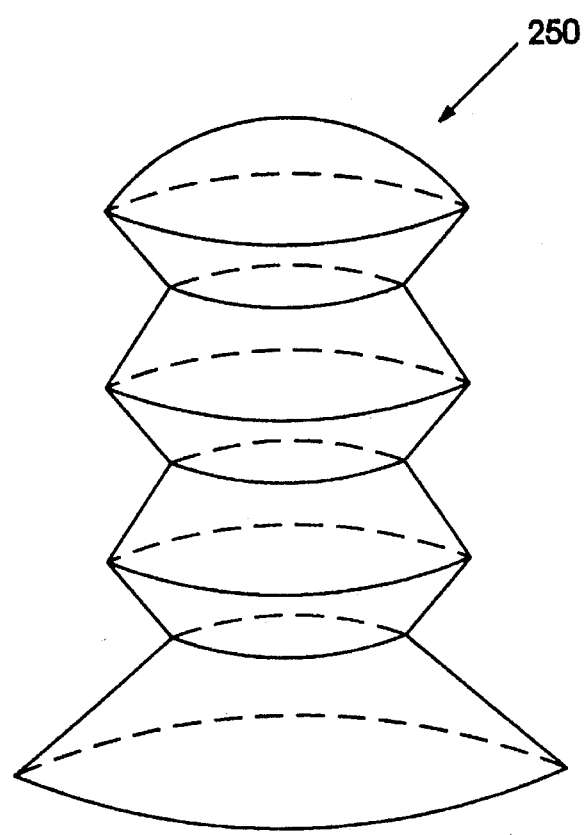
FIG. 7 is a perspective view of a device similar to that shown in FIGS. 5, 6 and 6A, but with additional length.

FIG. 7 is a perspective view of device 250, similar to the device shown in FIGS. 5, 6 and 6A, with the exception that device 250 has an extra set of disks in the expander section. This seven-disk structure is the preferred configuration for condoms. Device 250 has been partially expanded to reveal the accordion-like folds.

FIG. 8 is a side view of a device 300 with a glove 301 attached to an accordion-like folded section 302 to serve as the closed distal end of the device.

FIG. 9 is a pictorial view of the glove-like device 300 from FIG. 8 shown donned onto a human arm.

Figure 11:
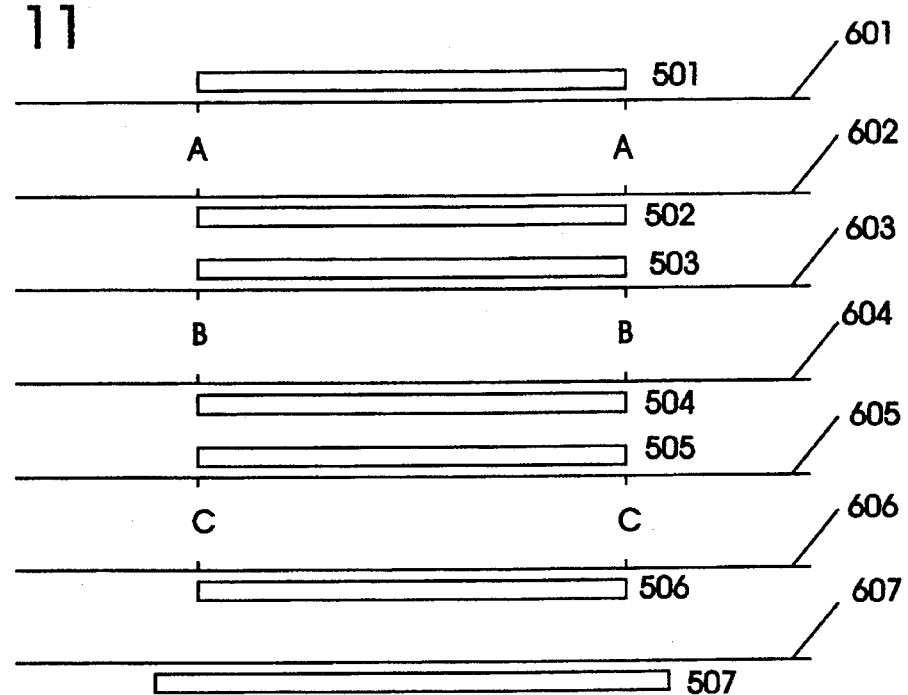
Figure 12:
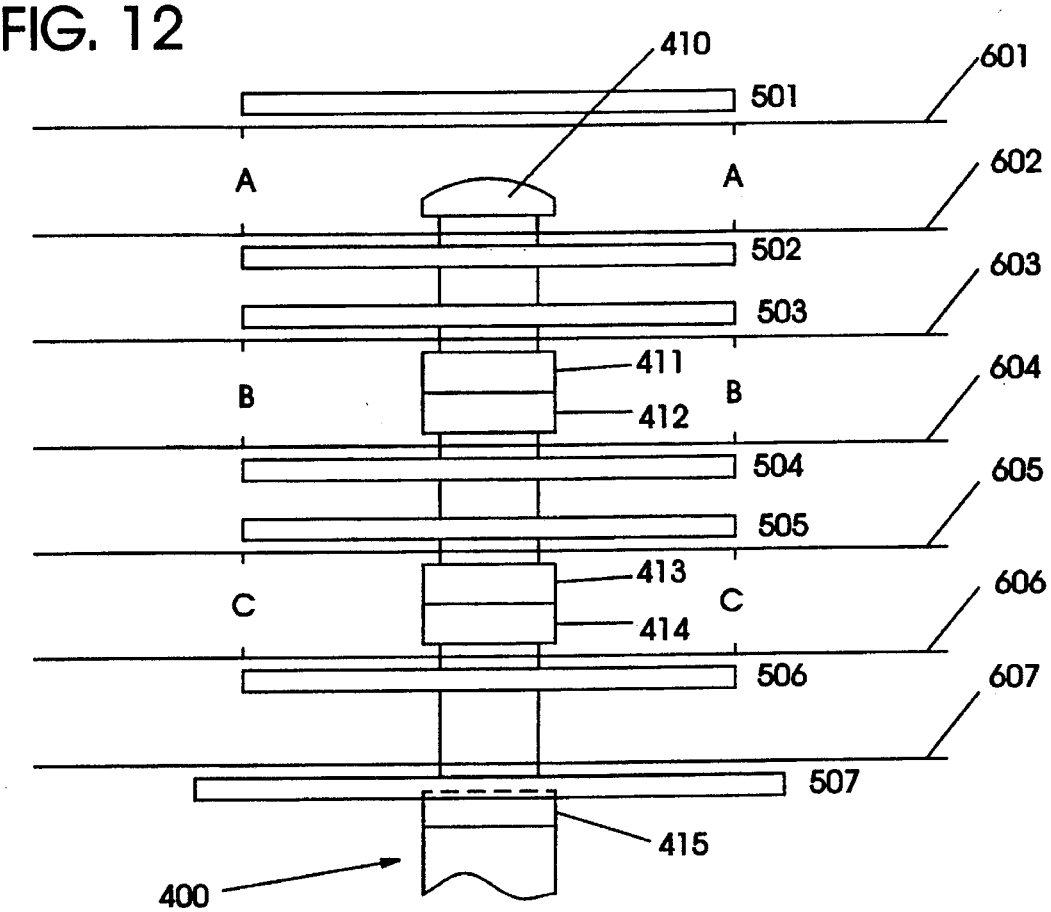
FIG. 12 is a side view of a mandrel and the sealing and cutting rings positioned to produce a prophylactic device from film pieces.

With reference to FIGS. 10–12, the description will now turn to a discussion of a preferred apparatus for producing the prophylactic devices of the invention. FIG. 10 is a side view of a generally cylindrical mandrel 400 that carries axially slidable flanges 411, 413, 415 and stationary flanges 410, 412, 414. Surface 420 of flange 410 mates with surface 421 of slidable flange 411 to create sealing surface a'. Surface 422 of flange 412 mates with surface 423 of slidable flange 413 to create sealing surface b'. Surface 424 of flange 414 mates with surface 425 of slidable flange 415 to create sealing surface c'.

The mandrel 400 of FIG. 10 can have the slidable flanges and fixed flanges reversed from that described above. Also, all flanges may be slidable, or selected flanges may slide, such as 411, 412 and 415. It is not important which flanges are slidable provided that the flanges mate to create a sealing surface to seal the aperture edges defined by the apertures in the disks.

The sealing surfaces a', b', c' of the flanges may incorporate any method of sealing that effects a joining of the film sections that is free of voids and holes. One preferred method is heat-sealing. Another preferred method is impulse sealing.

FIG. 11 is a side view of a set of sealing and cutting rings 501, 502, 503, 504, 505, 506, 507, with film pieces 601, 602, 603, 604, 605, 606, 607, threaded through. Film pieces 602, 603, 604, 605, 606, 607, have apertures formed therethrough by a previous step (not shown). The film portions are conveyed from the aperture forming operation by an indexing conveyor mechanism (not shown) as known in the art and delivered to the sealing and cutting station with the apertures aligned. Ring 501 mates with 502 to create seal A and cut the appropriately dimensioned disks from film pieces 601 and 602. Ring 503 mates with 504 to create seal B and cut the appropriately dimensioned disks from film pieces 603 and 604. Ring 505 mates with 506 to create seal C and cut the appropriately dimensioned disks from film pieces 605 and 606. Ring 507 cuts the appropriately dimensioned disk from film piece 607 by suitable thermal or mechanical means as are known in the art.

A preferred method of sealing at rings 501–506 is heat-sealing. With an appropriately formed die, a heat-seal and cut can be effected by the same die according to practices well known in the art. Another preferred method of sealing is impulse sealing. Impulse methods are also ideally suited to film cutting.

The sealing steps performed by mandrel 400 shown in FIG. 10 and the sealing and cutting steps performed by rings 501–507 shown in FIG. 11 are preferably performed concurrently. FIG. 12 shows the position of mandrel 400 and rings 501–507 just prior to sealing of the film sections 601–607 to each other and cutting of the disks from their carrier web of film. When the sealing and cutting steps are performed concurrently, a rapid manufacturing process ensues.

The manufacturing process begins as several layers of film are carried together by an indexing conveyor system that maintains registration between the layers of film. The film layers which require the apertures are cut in one step (for a single aperture size) or several steps (for multiple aperture sizes). The film layers, with the apertures in substantially concentric registration, are indexed to the next processing step (FIG. 12). In the next processing step, sealing and cutting rings 501–507 are positioned between the layers of film, above the top layer of film and/or below the bottom layer of film. Next, mandrel 400 containing the slidable flanges translates through the apertures. The diameter of the mandrel is substantially the same as the diameter of the apertures in the film layers. The slidable flanges on the mandrel are of slightly larger diameter than the diameter of the apertures. The slidable flanges pass through the apertures and the elastic nature of the film layers allows them to "snap" lock into the spaces between the slidable flanges. As mentioned above, the sealing and cutting can be accomplished in a single step or through several progressive steps. In the single step process, the slidable flanges on the mandrel mate and effect a seal around the peripheries of the top aperture to the second aperture, the third aperture to the fourth aperture, the fifth aperture to the sixth aperture, and so forth; concurrently, the sealing and cutting rings mate and effect a seal and cut, thus creating the end disk, which does not contain an aperture, and connecting the end disk to the first disk, which does contain an aperture, then the second and third disks are created and sealed together, then the fourth and fifth disk are created and sealed together, and so forth, with the last disk being cut and releasing the finished product from the layers of film. The product, if manufactured in a single step, is retained on the mandrel and can be ejected via air pressure through the mandrel tip or a vacuum tube above the mandrel. It will be appreciated that the mandrel has to be withdrawn to index the next sections of film, but the sealing and cutting rings may remain between the layers of film. Also the last disk at the proximal end of the prophylactic device can be cut in a separate, subsequent operation so that the finished product can be carried along on the film material to a next processing station. The next processing station might, for example, contain means for leak detection of the product or packaging of the product.

While the present invention has been described in connection with specific illustrated embodiments, it will be appreciated that modifications may be made without departing from the true spirit and scope of the invention.

That which is claimed is:

1. A prophylactic device formed of flexible film material and having an open proximal end and a closed distal end, said device comprising:
   (i) an odd number of superposed extension pieces, each extension piece having a peripheral edge and an aperture defining an aperture edge, said extension pieces being alternately sealed at their peripheral edges and their aperture edges to form a collapsible and extendable structure having a central opening therethrough and having a distally oriented end defined by a peripheral edge of said structure and a proximally oriented end defined by an aperture edge of said structure;
   (ii) a distal end piece formed without an aperture for providing a closed end for the device, said distal end piece including a peripheral edge;
   (iii) a proximal end piece with an aperture for providing an open end for the device, said proximal end piece defining an aperture edge;
   (iv) a seal joining the peripheral edge of the distal end piece and the peripheral edge of said structure; and
   (v) a seal joining the aperture edge of said structure and the aperture edge of the proximal end piece.

2. A prophylactic device according to claim 1 where the seals are heat seals.

3. A prophylactic device according to claim 1 where the seals are impulse seals.

4. A prophylactic device according to claim 1 where the proximal end piece is of greater area than the other pieces.

5. A prophylactic device according to claim 4 where the proximal end piece is triangular.

6. A prophylactic device according to claim 5 where the device is sized to fit a human penis.

7. A prophylactic device according to claim 1 where the distal end piece, the extension piece(s) forming the extension section and the proximal end piece are disk-shaped.

8. A prophylactic device according to claim 7 where the device is sized to fit a human penis.

9. A prophylactic device according to claim 1 where the film is selected from the group consisting of: polyurethanes, polyester urethanes, polyether urethanes, polystyrene-polyisoprene-polystyrene copolymers, polystyrene-poly(ethylene/butylene)-polystyrene copolymers, polyolefins, plasticized polyvinyl chloride, polyvinylidene chloride, polyesters, polyethers, polyamides, polyolefins, and polyvinylidene fluoride.

10. A prophylactic device according to claim 1 where the distal end piece is configured as a glove.

11. A prophylactic device according to claim 10 where the device is sized to fit a human arm.

12. A prophylactic device according to claim 1 where the device is sized to fit a human arm.

13. A prophylactic device according to claim 1 where the device is sized to fit a human leg.

14. A prophylactic device according to claim 1 where the device is sized to fit a human finger.

15. A prophylactic device having an open end and closed distal end and comprising:
   (i) a plurality of superposed disks formed of film material, each disk having a peripheral edge and an aperture defining an aperture edge, said disks being alternately sealed at their peripheral edges and their aperture edges to form a collapsible and extendable structure having a central opening therethrough;
   (ii) a distal end piece formed without an aperture for providing a closed end for the device, said distal end piece including a peripheral edge; and
   (iii) a seal joining the peripheral edge of the distal end piece and an edge of the disk at one of the ends of said collapsible and extendable structure.

16. A method for producing a prophylactic device of the type having a proximal open end and a distal closed end connected by a collapsible and expandable accordion-like structure, said method comprising the steps of:
   (i) forming an aperture in each of the first and second disks of a pair of disks of film material so that each first and second disk defines a peripheral edge and an aperture edge, with the aperture edges of the first and second disks having substantially the same size and configuration;
   (ii) providing a distal end piece of film material having no aperture and a peripheral edge of substantially the same size and configuration as the peripheral edge of the first disk of said pair;
   (iii) joining together the first and second disks by sealing them together at their respective aperture edges; and
   (iv) joining together the distal end piece and the first disk by sealing them together along their respective peripheral edges;
   whereby the distal end piece forms the closed distal end of the device and the peripheral edge of the second disk forms the open end of the device.

17. A method according to claim 16 including the step of joining together at least one additional pair of disks of film material to the peripheral edge of the second disk of the first mentioned pair of disks.

18. A method according to claim 17 wherein the prophylactic device is a condom and including the step of forming the condom with joined aperture edges sized to bear compressively on the human penis.

19. A method according to claim 16 including the step of joining together the aperture edges of the disks by first bringing the disks into spaced apart, superposed relationship with the apertures of the first and second disks concentrically aligned, followed by inserting a substantially cylindrical mandrel through the apertures and thereafter, with the film adjacent the apertures confined between a pair of spaced apart flanges carried on the mandrel, moving the flanges together to seal the aperture edges therebetween.

* * * * *